United States Patent
Schiffer et al.

(10) Patent No.: US 6,407,304 B2
(45) Date of Patent: Jun. 18, 2002

(54) PROCESS FOR THE ISOLATION OF HIGH BOILERS FROM THE CYCLOOLIGOMERIZATION OF 1,3-BUTADIENE

(75) Inventors: Thomas Schiffer, Haltern; Matthias May, Dorsten; Norbert Wilczok, Mülheim; Georg Oenbrink, Dülmen, all of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/772,966

(22) Filed: Jan. 31, 2001

(30) Foreign Application Priority Data

Feb. 3, 2000 (DE) .......................................... 100 04 758

(51) Int. Cl.$^7$ .............................. C07C 7/00; C07C 7/10
(52) U.S. Cl. ...................... 585/810; 585/809; 585/833; 585/864; 585/867
(58) Field of Search ................................ 585/809, 810, 585/833, 864, 867, 366

(56) References Cited

U.S. PATENT DOCUMENTS

| 3,658,926 A | 4/1972 | Morikawa |
| 3,865,888 A | 2/1975 | Akutagawa et al. |

FOREIGN PATENT DOCUMENTS

| DE | 1 283 836 | 11/1968 |
| DE | 1 906 361 | 8/1969 |
| DE | 1 942 729 | 2/1970 |
| DE | 2 063 348 | 7/1971 |
| GB | 1 287 252 | 8/1972 |
| JP | 46-8300 | * 3/1971 |

OTHER PUBLICATIONS

W. Brenner, et al., *Liebigs Ann. Chem.*, vol. 727, pp 161–182 (1969).
Chemical Abstracts, #78229, vol. 79, p. 449 (1973).
E.A. Ofstead, *Macromolecular Syntheses*, vol. 6, pp 69–75 (1977).
K. Saito, et al., *Bulletin of The Chemical Society of Japan*, vol. 52(11), pp 3192–3197 (1979).
Chemical Abstracts, #13184, vol. 81, p. 303 (1974).
Chemical Abstracts, #162460, vol. 97, p. 667 (1982).

* cited by examiner

Primary Examiner—Walter D. Griffin
Assistant Examiner—Tam M. Nguyen
(74) Attorney, Agent, or Firm—Oblon, Spivak, McClelland, Maier & Neustadt, P.C.

(57) ABSTRACT

A process for the isolation of high-boiling monomers from distillation residue formed in the cyclodimerization and/or cyclotrimerization of 1,3-butadiene after target products of cyclooctadiene, vinylcyclohexene and/or cyclododecatriene have been separated off, comprising extracting the distillation residue with a nonpolar or slightly polar solvent, separating off insoluble oligomers and polymers that have at least partly crystallized by mechanical separation, removing the extractant, and isolating the high-boiling monomers.

17 Claims, No Drawings

PROCESS FOR THE ISOLATION OF HIGH BOILERS FROM THE CYCLOOLIGOMERIZATION OF 1,3-BUTADIENE

BACKGROUND OF THE INVENTION

1. Field of the Invention

The invention relates to a process for the isolation of high boilers, in particular $C_{16}$ isomers, which are formed in the catalytic dimerization and trimerization of 1,3-butadiene.

2. Discussion of the Background

The reaction of 1,3-butadiene is carried out industrially over transition metal complexes or transition metal complex salts which are generally present as homogeneous solutions in a nonpolar organic phase. Suitable solvents are inert hydrocarbons such as benzene. The catalyst used is typically a transition metal of the 4th to 10th group of the Periodic Table in the oxidation state 0 and, if desired, a ligand such as a phosphine or a phosphite (W. Brenner, P. Heimbach, H. Hey, E. W. Muller, G. Wilke, Liebigs Ann. Chem. 727, 1969, 161-182; DE 12 83 836, Studiengesellschaft Kohle; DE 19 42 729, Mitsubishi Petrochemical Company Ltd.). Depending on the catalyst system, the main products formed are either the dimerization products cyclooctadiene (COD) and vinylcyclohexene (VCH) or the trimerization product cyclododecatriene (CDT). The selectivity of the reaction over the catalysts is high. It is generally over 90% in favor of the main component desired in each case.

After the reaction, the homogeneous catalyst is first decomposed and separated off. The decomposition is typically carried out by means of polar solvents such as monoalcohols having from 1 to 6 carbon atoms and water or by means of dilute acids. The reaction mixture (organic phase) is subsequently worked up by distillation. Here, unreacted 1,3-butadiene and solvent are returned to the reaction process; the various dimerization and trimerization products are subsequently separated from one another by distillation.

The bottoms from the column consist of a product mixture comprising oligomers and polymers of 1,3-butadiene as well as numerous high-boiling monomers having a defined molecular structure.

Typical monomers are compounds having from 12 to 30 carbon atoms, comprising a ring framework of from 6 to 24 carbon atoms and possibly one or more side chains. Important, nonlimiting representatives of such monomers are 3-(2-butenyl)-1,5,9-cyclododecatriene, 3-(3-butenyl)-1,5,9-cyclododecatriene and 3-(1-methylpropenyl)-1,5,9-cyclododecatriene as well as cyclohexedeca-1,5,9,13-tetraene.

Many of these macrocyclic monomers have been able to be isolated on a laboratory scale and their structure elucidated. Comprehensive descriptions may be found in DE 19 06 361 (Toyo Rayon Co.), GB 1 287 252 (Toray Industries), and in DE 20 63 348, US 3 658 926 and JP 48 019 304, cited according to CA 79:78229 (all Mitsubishi Petrochemical Co. Ltd.).

Difficulties generally occur in the selective synthesis of defined macrocycles. Studies have been carried out, for example, on the ring-opening metathesis of 1,5-cyclooctadiene over tungsten (E. A. Ofstead, Macromol. Synth. 1977, 6, 69), rhodium (K. Saito et al., Bull. Chem. Soc. Jpn. 1979, 52, 3192) or rhenium catalysts (US 3 865 888) and the oligomerization of 1,3-butadiene in which, if desired, linear dimers such as 1,3,7-n-octatriene may also be added (DE 20 63 348). All the methods give a product mixture comprising not only various macrocycles but also amounts of VCH, COD, CDT and polybutadienes. Only the selective syntheses of CDT and COD are used on an industrial scale.

In the selective synthesis of CDT or COD, a high-boiling, occasionally yellowish residue remains as bottoms from the distillation column in the customary form of work-up. At room temperature, this residue either remains a highly viscous liquid or solidifies to a wax-like solid, depending on composition. Distillation does not allow any further useful product to be isolated from this residue with a justifiable input of energy. The bottoms from the column are therefore generally incinerated as a waste product.

Extraction is a possible method of separating the high-boiling monomers and polymeric constituents. In GB 1 287 252, Example 1, this is carried out by addition of large amounts of acetone (500 g) relative to the reaction mixture (162 g of butadiene and 20 ml of toluene as solvent). In the other examples of GB 1 287 252, in which the reaction mixture is worked up and not only analyzed by gas chromatography, extraction with acetone as described in Example 1 is also employed.

In DE 19 06 361, not only toluene but also hexane, benzene, ether, i.e., diethyl ether, and tetrahydrofuran are mentioned as solvents. Here too, large amounts of acetone (500 g) relative to the solvent (in general from about 10 to 50 ml) are used as extractant. If larger volumes of solvent are used, viz., 200 ml of toluene (Example 10) or 250 ml of hexane (Example 15), the amount of solvent is reduced by distillation before acetone is added as extractant. However, in all cases the dimerization and trimerization products COD, VCH and CDT remain in the reaction mixture and are consequently also taken up in the acetone. JP 49 007 153 (cited according to CA 81:13184) also mentions acetone for the extraction.

However, application of the above-described extraction method to the selective synthesis of CDT or COD presents considerable difficulties. Thus, direct addition of acetone to the reaction mixture precipitates the polymeric or oligomeric components only very incompletely, if at all. It has also been found that the solvents described, in particular the aromatic and ether compounds, readily dissolve the oligomeric and polymeric components and thus make the extraction considerably more difficult.

Owing to the large amounts of CDT or COD which are also to be extracted in the selective synthesis of these compounds, the amount of acetone required for implementation of the prior art on an industrial scale would be tremendous.

SUMMARY OF THE INVENTION

It is therefore an object of the invention to provide a process for the isolation of high-boiling monomers from the distillation residue formed in the cyclodimerization and cyclotrimerization of 1,3-butadiene after the target products cyclooctadiene, vinylcyclohexene and/or cyclododecatriene have been separated off, which process does not have the abovementioned disadvantages.

It has now surprisingly been found that the high-boiling monomers can be readily extracted from the distillation residue using particular solvents without relatively large amounts of the oligomeric and polymeric components being dissolved at the same time. The insoluble oligomers and polymers can then be separated off predominantly in pulverulent, crystalline and surprisingly readily filterable form. With appropriate selection of the extractant, the extractant can easily be separated from the extracted monomers, preferably by distillation, and the monomers obtained in this way can then be isolated in pure form, preferably by means of vacuum distillation. (As used herein, the term "solvent" or "solvents" is intended to include solvent mixtures.)

The invention accordingly provides a process for the isolation of high boiling monomers from the distillation residue formed in the cyclodimerization and/or cyclotrimerization of 1,3-butadiene and separation of the target products, wherein the low boilers and solvent are separated off,
the desired target products such as cyclooctadiene or cyclododecatriene are isolated by distillation,
the distillation residue is extracted with a nonpolar or slightly polar solvent or solvent mixture,
insoluble oligomers and polymers (partly) crystallize and are separated off by a mechanical separation operation,
the extractant is removed, and
the high-boiling monomers are isolated.

DETAILED DESCRIPTION OF THE INVENTION

The invention is a process for the isolation of high boiling monomers from the distillation residue formed in the cyclodimerization and/or cyclotrimerization of 1,3-butadiene and separation of the target products, wherein the low boilers (e.g. unreacted 1,3-butadiene) and solvent are separated off,
the desired target products such as cyclooctadiene or cyclododecatriene are isolated by distillation,
the distillation residue is extracted with a nonpolar or slightly polar solvent or solvent mixture,
insoluble oligomers and polymers (partly) crystallize and are separated off by a mechanical separation operation (e.g. filtration),
the extractant is preferably removed as low boiler by distillation and
the high-boiling monomers are preferably isolated in pure form by vacuum distillation.

Studies on the extraction of the distillation residue showed that the extraction is very strongly dependent on the choice of solvent. It was surprisingly found that both nonpolar solvents such as unbranched or branched aliphatic hydrocarbons, preferably having from 5 to 10 carbon atoms (e.g. pentane, hexane and octane), cycloaliphatic hydrocarbons having preferably from 5 to 10 carbon atoms (e.g. cyclohexane), unbranched or branched olefinic and cycloolefinic hydrocarbons having preferably from 5 to 12 carbon atoms (e.g. cyclooctene) and also some slightly polar, aprotic solvents such as branched or unbranched aliphatic and cycloaliphatic ketones and aldehydes preferably having a total of from 3 to 12 carbon atoms and their mixtures are very suitable as extractants. Preferred solvents from the group of ketones are acetone and 2-butanone (methyl ethyl ketone). Supercritical gases such as carbon dioxide and ethane are also suitable in principle as extractants.

It has surprisingly been found that the aromatics, alcohols and ethers used in the prior art are, in contrast, less well suited. In general, the solubility of the monomers in alcohols is too low. In aromatics and ethers, the oligomers and polymers dissolve too well.

In the cyclodimerization or cyclotrimerization of 1,3-butadiene, the process of the present invention provides for volatile components to be separated off first and the respective main product to be freed of high-boiling components by being taken off at the top in the distillation. The bottoms from the column are then a viscous mixture of high boilers which cannot be distilled further at justifiable cost. The bottoms are then, according to the invention, digested with a solvent or solvent mixture (extractant/extractant mixture), preferably at elevated temperature under reflux. Here, the heat of the bottoms from the column can be exploited for heating the extractant. After digestion and cooling, the insoluble components are separated off by means of a mechanical separation operation such as a filtration or sedimentation. The solvent or solvent mixture is preferably separated from the extract by distillation and can be reused in the extraction process. In particular cases, a chromatographic separation, e.g., preparative liquid chromatography (HPLC), can also be carried out. This leaves a high-boiling oil which is low in oligomers and polymers and can then be further purified by distillation, preferably under reduced pressure, or by means of suitable chromatographic separation processes.

The solvent or solvent mixture for the extraction is chosen so that the monomeric substances are largely leached from the bottoms while a major part of the oligomeric and polymeric components remains insoluble. Choice of the correct extractant also makes it possible for the insoluble fraction of the bottoms to begin to crystallize during digestion. Uniform cooling of the extraction mixture allows the crystallization to be increased, as a result of which the proportion of dissolved polymers in the extract is further reduced.

The precipitate obtained consists mainly of oligomers and polymers of 1,3-butadiene. It is generally colorless and at least partly crystalline. When the correct extractant and the correct temperature are chosen, it is no longer sticky or only slightly sticky and can thus easily be separated off, for example by means of a filter or a suction filter. When cooling the extraction mixture, a lower temperature limit results from either the solubility of the monomeric components in the extractant becoming too low or the monomers freezing out from the mixture. In both cases, this is clearly indicated by the extraction mixture becoming milky and the precipitate conglutinating. The precise temperature limit is, inter alia, in each case dependent on the extractant and the composition of the high boilers in the bottoms. It is usually in the range from +20 ° C. to −10° C.

The boiling range of the solvents used for the extraction should be from 35 to 130° C. A particularly preferred boiling range is from 50 to 105° C. If desired, the extraction can also be carried out under superatmospheric pressure.

In the case of solvents having boiling points above 110° C., the oligomeric and polymeric components melt, which prevents crystallization of these components during digestion under reflux. In the case of solvents having boiling points below 35° C., the boiling point of the extractant is too close to the lower temperature limit for solubility of the high-boiling monomers. The desired properties of the extractant can also be set particularly well by combining two or more solvents.

As a further secondary effect of the process of the invention, it is found that residual amounts of the main product which can no longer be isolated by distillation from the bottoms from the column can be made accessible by extraction. In this way, further target product (main product) from the cyclodimerization or cyclotrimerization can be isolated.

If the high boilers originate, for example, from the bottoms from the cyclododecatriene column, further cyclododecatriene can be isolated by means of the extraction.

Potential application areas for these high-boiling monomers are in the perfume and fragrance industry, for example, in the synthesis of macrocyclic ketones (JP 57 021 254, Takasago Perfumery Co., cited in CA 97:162 457). However, a main application for these compounds is as crosslinkers in synthetic rubbers.

Having generally described this invention, a further understanding can be obtained by reference to certain specific examples of the inventive process, which are provided herein for purposes of illustration only and are not intended to be limiting unless otherwise specified.

EXAMPLES

Examples of Extraction

In the following examples, a distillation residue from the preparation of cyclododecatriene was used. This was in each case taken up in 400 ml of extractant and digested under reflux for 1 hr. The mixture was subsequently cooled to 20° C. or 4° C., allowed to stand overnight and subsequently filtered. The filtrate was freed of the extractant and filtrate and filter cake were weighed. The losses between initial and final weights were caused by adhesion to the laboratory apparatus used. The results are summarized in Table 1.

Example of Distillation 411.1 g of filtrate from Experiment 6 were distilled under reduced pressure via a 1 m packed column. A further 7.0 g of CDT isomers (colorless oil, 78–85° C./2 mbar) and also 107.3 g of a mixed fraction (light-yellow oil, 110–122° C./2 mbar) and 238.29 g of a $C_{16}$ main fraction (colorless oil, 124–126° C./2 mbar) were able to be isolated. The remainder stayed as a dark residue at the bottom. Analysis of the $C_{16}$ fraction indicated 3-(2-butenyl)1,5,9-cyclododecatriene as one of the main products.

What is claimed is:

1. A process for the isolation of high-boiling monomers from distillation residue formed in the cyclodimerization and/or cyclotrimerization of 1,3-butadiene after target products of cyclooctadiene, vinylcyclohexene and/or cyclododecatriene have been separated off, comprising:
    extracting the distillation residue with an extract which is a nonpolar solvent selected from the group consisting of an unbranched or branched aliphatic hydrocarbon, a cycloaliphatic hydrocarbon, an unbranched or branched olefin hydrocarbon, and an unbranched or branched cycloaliphatic hydrocarbon or a slightly polar solvent selected from the group consisting of a branched or unbranched aliphatic ketone, branched or unbranched cycloaliphatic ketone, a branched or unbranched aliphatic aldehyde, and a branched or unbranched cycloaliphatic aldehyde, thereby obtaining an extract and an extraction residue,
    separating off by mechnical separation oligomers and polymers which are insoluble in said extractant and that hace at least partly crystallized,
    isolating the high-boiling monomers from a residue of the extract, after distillative removal the extractant.
2. The process as claimed in claim 1, wherein the extractant has a boiling point in the range from 35° C. to 130° C.
3. The process as claimed in claim 2, wherein the extractant has a boiling point in the range from 50° C. to 105° C.
4. The process as claimed in claim 1, wherein the extractant is acetone.
5. The process as claimed in claim 4, wherein the extractant is 2-butanone.
6. The process as claimed in claim 1, wherein the mechanical separation comprises sedimentation.
7. The process as claimed in claim 1, wherein the mechanical separation comprises filtration.
8. The process as claimed in claim 1, wherein further target product of the cyclodimerization or cyclotrimerization is isolated from the extract.

| No. | Extractant (bp in ° C.) | Residue weighed in (g) | Filtration at (° C.) | Weight of filtrate (g) | Weight of precipitate (g) | Appearance of filtrate | Appearance of precipitate |
|---|---|---|---|---|---|---|---|
| 1 | n-Pentane (36) | 151.3 | 4 | 120.4 | 22.1 | yellow oil 1) | colorless, slightly sticky |
| 2 | n-Hexane (68) | 161.9 | 20 | 147.7 | 8.34 | yellow oil 1) | colorless, pulverulent |
| 3 | n-Heptane (98) | 155.1 | 20 | 128.7 | 20.5 | yellow oil | colorless, slightly sticky |
| 4 | Petroleum ether (~100) | 171.7 | 20 | 158.2 | 9.4 | yellow oil 1) | colorless, pulverulent |
| 5 | Petroleum ether (~100) | 148.2 | 4 | 83.7 | 54.2 | yellow oil | colorless, sticky |
| 6 | Acetone (56) | 134.1 | 20 | 75.6 | 52.4 | yellow oil | colorless, sticky |
| 7 | 2-Butanone (79) | 166.4 | 20 | 144.9 | 11.8 | yellow oil 1) | colorless, pulverulent |
| 8 | 2-Butanone (79) | 125.6 | 4 | 103.9 | 16.0 | yellow oil | colorless, pulverulent |
| 9 | 3-Pentanone (102) | 150.9 | 4 | 96.3 | 40.1 | yellow oil | colorless, pulverulent |
| 10 | Cyclopentanone (129) | 154.3 | 4 | 122.3 3) | 58.7 | yellow oil | colorless, slightly sticky |
| 11 | Propionaldehyde (48) | 150.8 | 4 | 53.0 | 97.2 | yellow oil | yellow, pulverulent |
| | | | Comparative examples for less suitable solvents | | | | |
| 12 | Isopropanol (82) | 154.6 | 20 | 64.68 | 84.31 | yellow oil | colorless, sticky |
| 13 | Toluene (110) | 163.2 | 20 | — | — | yellow oil | – 2) |
| 14 | THF | 148.3 | 20 | — | — | yellow oil | – 2) |

1) Filtrate clear; a fine, colorless precipitate is formed on taking off the extractant
2) Completely dissolved, therefore no precipitate can he separated off
3) Still Contains about 10% of extractant The disclosure of German application 100 04 758.0, filed Feb. 3, 2000, of which priority is claimed under 35 U.S.C. 119, is hereby incorporated by reference.

9. The process as claimed in claim 1, wherein the high-boiling monomers isolated comprise $C_{16}$ compounds.
10. The process as claimed in claim 4, wherein the mechanical separation comprises sedimentation.

11. The process as claimed in claim 4, wherein the mechanical separation comprises filtration.

12. The process as claimed in claim 4, wherein further target product of the cyclodimerization or cyclotrimerization is isolated from the extract.

13. The process as claimed in claim 4, wherein the high-boiling monomers isolated comprise $C_{16}$ compounds.

14. The process as claimed in claim 5, wherein the mechanical separation comprises sedimentation.

15. The process as claimed in claim 5, wherein the mechanical separation comprises filtration.

16. The process as claimed in claim 5, wherein further target product of the cyclodimerization or cyclotrimerization is isolated from the extract.

17. The process as claimed in claim 5, wherein the high-boiling monomers isolated comprise $C_{16}$ compounds.

* * * * *